(12) United States Patent
Fassina et al.

(10) Patent No.: US 6,426,401 B1
(45) Date of Patent: Jul. 30, 2002

(54) PHARMACEUTICAL COMPOSITION CONTAINING AN INHIBITOR OF IMMUNOGLOBULIN-RECEPTOR INTERACTION

(75) Inventors: Giorgio Fassina, Milan; Sandro De Falco, Naples, both of (IT)

(73) Assignee: Tecnogen S.C.p.A., Piana di Monte Verna (IT)

( * ) Notice: Subject to any disclaimer, the term of this patent is extended or adjusted under 35 U.S.C. 154(b) by 0 days.

(21) Appl. No.: 09/319,273

(22) PCT Filed: Dec. 11, 1997

(86) PCT No.: PCT/EP97/07143

§ 371 (c)(1),
(2), (4) Date: Jul. 2, 1999

(87) PCT Pub. No.: WO98/26794

PCT Pub. Date: Jun. 25, 1998

(30) Foreign Application Priority Data

Dec. 16, 1996 (IT) .......................................... MI96A2628

(51) Int. Cl.$^7$ ................................................. C07K 5/08
(52) U.S. Cl. ............................. 530/331; 514/7; 514/18; 530/329; 530/330; 530/331
(58) Field of Search ....................... 514/18, 7; 530/330, 530/331

(56) References Cited

U.S. PATENT DOCUMENTS 4,628,045 A * 12/1986 Hahn ........................... 514/17

5,880,259 A * 3/1999 Fassina ....................... 530/326

FOREIGN PATENT DOCUMENTS

| WO | 86/01211 | * | 2/1986 |
| WO | 96/01643 | * | 1/1996 |

* cited by examiner

*Primary Examiner*—Christopher S. F. Low
*Assistant Examiner*—David Lukton
(74) *Attorney, Agent, or Firm*—Oblon, Spivak, McClelland, Maier & Neustadt, P.C.

(57) ABSTRACT

The present invention relates to a pharmaceutical composition comprising a biologically effective amount of a peptide of formula (I)

$$(H_2N-X_1-CO-Thr-NH-X_2-CO)_n-R \qquad (I)$$

where $NH-X_1-CO$ and $NH-X_2-CO$ which are different from one another, are residues of tyrosine or arginine, in L or D configuration, where the hydroxy group of threonine and the guanidine moiety of arginine may be protected by a group conventionally used in peptide chemistry for protecting the hydroxy group and the guanidine moiety, respectively, n is 2, 3, or 4, R is a group capable of forming a dimeric, trimeric, or tetrameric peptide, and a pharmaceutically acceptable inert carrier.

14 Claims, No Drawings

PHARMACEUTICAL COMPOSITION CONTAINING AN INHIBITOR OF IMMUNOGLOBULIN-RECEPTOR INTERACTION

This invention relates to a pharmaceutical composition which comprises a peptide capable of inhibiting the interaction between immunoglobulins and their receptors.

BACKGROUND

It is known that the interaction between immunoglobulins (Igs) and their related receptors placed on the cellular surface, induces a series of different reactions depending on the ig isotype recognized by the receptor. For example, the binding on macrophages of immunoglobulins G to their related receptors FcgR leads to endocytosys, to complex antigen antibody lysosomal degradation and to secretion of potent inflammation mediators like prostaglandins, leukotriens, oxygen intermediates and neutral proteases (Unkeless et al., 1981, J.Exp.Med.171, 597–611).

Is also known that immunoglobulins interact with their related receptors by the constant portion, named Fc, independently of the antibody antigen specificity (Fridman et al., 1992, Immunol. Rev. 125, 49–76).

Synthetic compounds capable of interfering with the immunoglobulin/receptor interaction are not yet available. Only the soluble forms of the natural receptors, named sFcR, obtained as recombinant products, through genetic engineering techniques, are actually capable to act as inhibitors of this important interaction (Sautes et al., 1994, J. Chrom. 662, 197–207).

It is therefore apparent that the inhibition of the interaction between immunoglobulins and receptors is an important therapeutic approach in all those cases where it is important to control the effects of an Ig over-production and when the effects generated by the Ig/receptor recognition are negative for the cell cycle.

For example, in the multiple myeloma, an incurable tumor disease since it is resistant to standard chemotherapy, experimental data have indicated that a flanking immunotherapy based on the administration of soluble receptors for Fc reduces tumor cells growing and immunoglobulins secretion (Hoover et al., J. Clin. Invest. 95, 241–247).

In turn, in acquired immunodeficiency (AIDS), in patients sera are present antibodies that increase virus infectivity interacting with the respective cellular receptors (Homsy et al., 1989, Science 244, 1357–1360) and consequently, a therapy based on the administration of molecules capable of interfering with receptors that interact with Igs is of remarkable therapeutic importance for HIV virus infectivity.

Also in diseases of inflammatory origin, as the rheumatoid arthritis, the event that leads to the pathologic condition is the immunoglobulins interaction with the corresponding cellular receptors (Fearon & Wong, 1983, Ann. Rev. Immunol. 1, 243) and, as in the previous cases, a treatment based on the administration of molecules capable of interfering with the recognition Ig/receptor can give notable therapeutic benefits.

Even allergic reactions are triggered by the interaction of immunoglobulins, in this case of the E class, with the corresponding cellular receptors.

Given the wide therapeutic application spectrum and the pathology sternness there is therefore a great demand of synthetic compounds, and therefore free of contaminants of biological origin and of low cost, that could be capable of interfering with the interaction between immunoglobulins and the related receptors.

Now it has been found that these properties are owned by a peptide of formula (I):

$$(AA_1\text{-Thr-}AA_2\text{-})_n\text{-R} \qquad (I)$$

wherein $AA_1$ and $AA_2$ different one another, are an amino acidic residue of tyrosine and arginine, in the L or D configuration, wherein the hydroxy group of threonine and the guanidine moiety of arginine may be protected by a compound conventionally used in peptide chemistry for protecting the hydroxy group and the guanidine moiety, respectively, n is 2,3,or 4, and R is a group capable of forming a dimeric, trimeric, and respectively tetrameric peptide.

The preparation of these compounds has been described in the european patent application n. 96201706.7 of 19.06.1996 in the name of the same applicant. Said application, not yet published, describes the properties of the compounds as immunoglobulins ligands.

BRIEF SUMMARY OF THE INVENTION

Therefore, it is a first object of this invention to provide a pharmaceutical composition comprising a biologically effective amount of a peptide of formula (I):

$$(AA_1\text{-Thr-}AA_2\text{-})_n\text{-R} \qquad (I)$$

wherein $AA_1$ and $AA_2$, different from one another, are an amino acid residue of tyrosine and arginine, in L or D configuration, wherein the hydroxy group of threonine and the guanidine moietly of arginine may be protected by a compound conventionally used in peptide chemistry for protecting the hydroxy group and the guanidine moiety, respectively, n is 2, 3, or 4.

R is a group capable to form a dimeric, trimeric, and respectively tetrameric peptide, and at least a pharmaceutically acceptable inert ingredient.

Preferably n is 4.

Each amino acid of the compound of formula (I) can have L or D configuration.

In the present description and in the claims, the terms "dimer" "trimer" and "tetramer" intend to mean peptides comprising two, three and respectively four sequences $AA_1$-Thr-$AA_2$- where $AA_1$ and $AA_2$ have the above mentioned meanings.

A typical example of a suitable group for forming a dimer (n=2) is a lysine residue. A typical example of a suitable group for forming a trimer (n=3) is a dipeptide lysine-lysine of formula Lys-Lys. Typical examples of suitable groups for forming a tetramer (n=4) are a branched tripeptide of formula Lys-Lys(ε2Lys) and a branched tetrapeptide of formula Gly-Lys-Lys(εLys).

A typical example of a tetramer of formula (I) has the following formula $$(AA_1\text{-Thr-}AA_2\text{-})_4\text{-}(Lys)_2\text{-Gly-OH} \qquad (IA)$$

wherein $AA_1$ and $AA_2$ have the above mentioned meanings, and wherein the hydroxy group of threonine and tyrosine and the guanidine moiety of arginine may be protected by a compound conventionally used in peptide chemistry for protecting the hydroxy group and the guanidine moiety, respectively.

Many group useful for protecting the hydroxy group are reported in the literature (Grant G. A. "Synthetic peptides: a users guide" Freeman, N.Y., 1992).

Typical examples of said protecting groups are the ter-butyl (tBu) (La Joie G., Crivici A., Adamson J. G., "Synthesys" 571–572 (1990) and the benzyl group (Yojima "Tetrahedron" 44: 805–819 (1988)).

Many groups useful for protecting the guanidine moiety of arginine are also known from the literature (Grant G. A. "Synthetic peptides: a user's guide" Freeman, N.Y., 1992).

Typical examples of said protecting group are: 2,2,5,7,8-pen-tamethylcroman-6-sulphonyl (Pmc) and 4-methoxy-2,3,6-trimethylbenzene (Mtr) (Ramage & Green "Tetrahedron Letters", 28, 2287 (1987); Fujiino et al. "Chem. Pharm. Bull., 29, 2825, (1981).

Specific examples of compound of formula (IA) are

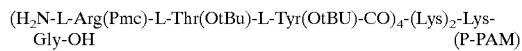
(P-PAM)

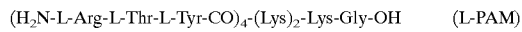
(L-PAM)

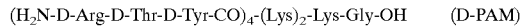
(D-PAM)

As described in detail below, the biological activity of formula (I) peptides has been assayed in the inhibition of the binding between immunoglobulin and receptor (Ig-FcR) and in the rosettes formation inhibition between sheep red blood cells (SRBC) derivatized with human IgG and U937 cells and the result was that compounds of formula (I) produce on Ig receptor the same interaction as Ig and that said interaction is dose-dependent. In addition, the biological activity of the compounds of formula (I) has been evaluated in vivo by passive cutaneous anaphylaxis assay, which represents the animal model for the study of antiallergic compounds.

In mouse acute toxicity tests the compounds of formula (I) are well tolerated either by oral or by intravenous administration.

Typical examples of pathologic conditions that may benefit from the treatment with a pharmaceutical composition according to this invention are those where it is useful or necessary to interfere on the interaction between Ig and their receptors. Typical examples of these pathological conditions are rheumatoid arthritis, and allergic reactions.

Preferably, the pharmaceutical compositions according to this invention are prepared in a suitable dosage form comprising an effective dose of at least one compound of formula (I) and at least a pharmaceutically acceptable inert ingredient.

Example of suitable dosage form are tablets, capsules, coated tablets, granules, solutions and syrups for oral administration, ointments and medical patches for topic administration; suppositories for rectal administration and sterile solutions for injectable, aerosolic and ophthalmic administration.

The dosage forms may also contain other conventional ingredients like: preservatives, stabilizers, surface-active agents, buffers, salts to regulate osmotic pressure, emulsifiers agents, sweeteners, colouring agents, flavouring agents and the like.

If required for particular therapies, the pharmaceutical composition of this invention may contain other active pharmacological ingredients where concomitant administration is therapeutically useful.

The amount of peptide of formula (I) in the pharmaceutical composition of this invention may vary in a wide range depending on known factors such as, for example, the type of disease to be treated, the disease severity, the patient weight, the dosage form, the route of administration chosen, the number of daily administrations and the efficacy of the selected peptide of formula (I).

Typically, the amount of peptide of formula (I) in the pharmaceutical composition of this invention will be such as to enssure an administration level of from 1 to 200 mg/Kg/day, preferably of from 2 to 50 mg/Kg/day.

The dosage forms of the pharmaceutical composition of this invention can be prepared according to techniques well known to the pharmaceutical chemist comprising mixing, granulation, compression, dissolution, sterilization and the like.

EXAMPLES

Example 1

In case of P-PAM, L-PAM and D-PAM peptides it has been evaluated their capability of inhibiting the interaction between human IgG or IgA and their respective receptors Fcγ and Fcα.

For this purpose, it has been developed an inhibition assay of the binding between human immunoglobulins (Ig) IgG and IgA and their receptors on U937 human cell line plasma-membrane.

U937 cell line (Sundstrom, C. and Nilsson K., Int. J. Cancer, 17, 565, 1976) supplied by ECACC (Cat. n. 87010802) derives from a hysticytic lymphoma and is one of the few human cell lines that express many monocyte-like properties shown by cells of hystoicytic origin. Therefore, it has been widely employed in the study of the interaction between Ig and Fc receptors (FcR) (McCool D. et al., J. Immunol, 135, 1975–1980, 1985; Raychaudhuri G. et al., Mol. Immunol., 22, 1009–1019,1985; Burton D. R. et al., Mol. Immunol., 25, 1175–1181, 1988).

The IgG receptors FcgRI and FcgRII (Looney R. et al., J. Immunol., 136, 1641, 1986) and IgA receptors Fca (Monteiro R. C., et al., J. Exp.Med., 171, 597–613, 1990) are constitutively express by this cell line.

The first step for the assay set up has been the preparation of plasma-membranes from U937 cells. This preparation has been obtained following the protocol of Hubbard A. L. et al. (J. Cell. Biol., 96, 217–229, 1983), based on the controlled cells homogenization except that this homogenization has been done with a Dounce apparatus and the subsequent purification of plasma-membrane fractions on sucrose density gradient.

The cells, after cultivation following the provider conditions, have been harverest and centrifuged (10', 4° C., 100×g), washed three times with cold D-PBS and centrifuged again. The cell pellet obtained (1.5 g) has been weighted and suspended in 4 ml of STM 0.25M [0.25M sucrose in TM (5mM Tris-HCl pH 8, 0.5mM $MgCl_2$)].

The suspension has been stored at 4° C. for 10'.

The cells have been homogenized in Dounce [(40 passages with A pestle (large) and as many with B pestle (small)], checking at the microscope the cells breaking, and centrifuged (4° C., 10', 280×g) to remove intact cells, nuclei and cellular debris.

After supernatant recovery, the pellet has been resuspended in ½ of STM initial volume and treated with 10 passages of A pestle in Dounce. The suspension has been centrifuged (4° C., 10', 280×g). The supernatant has been recovered and pooled with that obtained in the above step. The supernatants pool has been centrifuged (10', 4° C., 100×g).

The pellet obtained has been resuspended in 0.25M STM and the solution density has been adjusted to 1.18 gr/cm$^3$ by adding 2M STM (2M Sucrose in TM). On the obtained solution 0.25M STM has been stratified and then ultracentrifuged (1h, 4° C., 78000×g).

Plasma-membrane fraction has been recovered from the interface between the two sucrose gradient phases.

The second phase for the competition assay set up was human Ig biotinylation (IgG, Sigma Cat. No. I-4506 and IgA, Sigma Cat. No. I-0663). 0.5 ml of a 2 mg/ml immunoglobulins solution in 150 mM sodium phosphate buffer (PBS) have been mixed with 0.5 ml of 6 mg/ml biotin solution (Biotinamidocaproate N-Hydroxysuccinimmide Ester Sigma Cat. No. B-2663) in H$_2$O/EtOH 1:1. The obtained solution has been incubated for 15 hours at room temperature, under stirring. Biotin in excess has been later removed by dialysis against 50 mM phosphate buffer pH 7.5.

To carry out the inhibition of Ig/Fc binding assay, there have been set up the conditions by linear binding assays between biotinylated Ig and receptors present on plasma-membrane preparation.

Microplates for ELISA determination (Falcon Cat. No. 3912) have been treated with plasma-membrane obtained from U937 cells in variable concentrations between 0.1 and 10 µg/ml (referred to the total proteins in the plasma-membrane preparation) in PBS, 100 µl/well, for 15 hours at 4° C. The plates have been washed 5 times with PBS and the saturation of a specific sites has been done adding, for each well, 180 µl of a PBS solution containing 3% of bovine serum albumin (BSA, Sigma Cat. No. A-9418).

After 1 hour and 30' at room temperature, the plates have been washed 5 times with PBS-T (PBS-Tween 0.05%) and each well has been filled with 100 µl of solutions containing biotinilated Ig at variable concentrations between 0.02 and 2 µg/ml in PBS-BSA 0.5%.

After incubation of 1 h 30' at 37° C., a solution of streptavidin derivatized with peroxidase has been added (Sigma, Cat. No. S-5512) diluted 1:1000 in PBS-BSA 0.5%, 100 µl/well. After 1 h incubation at 37° C., the plates have been washed 5 times with PBS-T and each well has been filled with 100 µl of a 2,2'-azino-bis(3-ethylbenzthiazoline-6-sulfonic acid) (Sigma, Cat. No. A-9941) in phosphate buffer pH 5 and 0.012% hydrogen peroxide.

After about 30' the absorbance at 405 nm of each well has been determined by a plate reader (Merck, Mod. Mios) and the results are shown in TABLE 1.

TABLE 1

Linear binding between Human biotinylated IgG or IgA and plasma membrane (PM) preparation obtained from U937 cell-line

| | OD 405 nm | | |
|---|---|---|---|
| µg/ml | U937 PM 0.1 µg/ml | U937 PM 1 µg/ml | U937 PM 10 µg/ml |
| h-IgG Biotinilated | | | |
| 0.02 | 0 | 0.03 | 0.105 |
| 0.1 | 0.01 | 0.1 | 0.385 |
| 0.2 | 0.03 | 0.141 | 0.58 |
| 1 | 0.14 | 0.283 | 0.98 |
| h-IgA Biotinilated | | | |
| 0.02 | 0 | 0 | 0.035 |
| 0.1 | 0 | 0.014 | 0.144 |

TABLE 1-continued

Linear binding between Human biotinylated IgG or IgA and plasma membrane (PM) preparation obtained from U937 cell-line

| | OD 405 nm | | |
|---|---|---|---|
| µg/ml | U937 PM 0.1 µg/ml | U937 PM 1 µg/ml | U937 PM 10 µg/ml |
| 0.2 | 0 | 0.044 | 0.245 |
| 1 | 0.093 | 0.156 | 0.502 |

Data reported in Table 1 show that either IgG and IgA bind receptors present in the plasma-membrane preparation in a dose dependent manner.

The inhibition Ig/Fc assay has been carried out using U937 plasma-membrane at 10 µg/ml concentration for immobilization on plate and biotinylated Ig at 0.4 µg/ml concentration.

IgGs have been incubated with peptides of this invention (L-PAM, D-PAM and P-PAM) and two controls, namely peptides Arg-Thr-Tyr in L configuration (named CON-L) and in D configuration (named CON-D), at concentrations between 1 to 500 µg/ml (Table 2), whereas for IgA the inhibition assays have been carried out in similar conditions with L-PAM and CON-L peptides (Table 3).

TABLE 2

IgG-FcR binding inhibition

| Inhibitors | IgG | L-PAM | D-PAM | P-PAM | CON-L | CON-D | BSA |
|---|---|---|---|---|---|---|---|
| 1 | 94.7 | 99 | 97.7 | 94 | 96.7 | 93 | 107 |
| 10 | 78 | 88.5 | 96.9 | 96.5 | 93.8 | 91 | 104 |
| 100 | 30 | 84 | 66 | 80 | 98.7 | 100 | 97.9 |
| 250 | 9.9 | 45 | 34.5 | 29 | 99.5 | 100 | 97.1 |
| 500 | 3.6 | 17.2 | 22.5 | 8 | 102 | 104 | 97.9 |
| µg/ml | | | | B/Bo | | | |

B/B0 means the inhibition percentage calculated dividing the values, in terms of OD, obtained in presence of competitors, by those obtained in absence of competitors.

TABLE 3

IgA/FcR binding inhibition

| Inhibitors | IgA | L-PAM | P-PAM | CON-L | BSA |
|---|---|---|---|---|---|
| 1 | 96.1 | 96 | 88 | 102 | 102 |
| 10 | 83.1 | 82.2 | 85 | 100 | 98 |
| 100 | 27.25 | 47.1 | 64 | 96 | 100 |
| 250 | 5.35 | 28.1 | 30 | 90 | 96 |
| µg/ml | | | B/Bo | | |

B/B0 has the above mentioned meaning.

Data reported in Table 2 and 3 show that L-PAM, D-PAM and P-PAM produce, in a dose-dependent manner, the same interaction level as IgG. This inhibition is specific because both the control (BSA) and the two peptides CON-L and CON-D are unable to inhibit this interaction.

In the same way, L-PAM and P-PAM peptides specifically inhibit the interaction IgA-FcR, whereas both BSA and CON-L are unable to produce the same effect.

Moreover, it has been evaluated the type of inhibition produced on the rosettes formation between SRBC derivatized with human IgG and U937 cells by the compounds of this invention.

Example 2

The trial has been carried on L-PAM and D-PAM peptides with the assay of rosettes formation inhibition between sheep red blood cells (SRBC) derivatized with human IgG and U937 cells (prepared as described above).

Rosettes formation assay has been performed in accordance with the protocol of Lund J. et al. (FASEB J., 9, 115–119, 1995) modified as follows.

The derivatized SRBC have been prepared using SRBC-tanned (tannic acid pretreated SRBC, Sigma Cat. No. R-8128) and human IgG (Sigma Cat. No. I-4506) following the provider protocol. At the end of derivatization IgG-SRBC have been resuspended in a solution containing 0.1% Bovine Serum Albumin (BSA, Sigma Cat. No. A-9418) in DPBS (Sigma, Cat. No. D-5527).

$2.5 \times 10^5$ U937, taken from a culture of $7.5 \times 10^5$ cell/ml density, have been centrifuged for 5 minutes at 80×g, resuspended in 50 µl of DPBS-BSA 0.1% and incubated with 50 µl of DPBS-BSA 0.1% containing $2.5 \times 10^7$ SRBC-IgG; a ratio U937/SRBC-IgG 1:100 has been used.

After 30 minutes at 25° C. rosettes have been counted, and more particularly U937 having 4 or more SRBC bound on the surface. In these conditions it has been discovered that, on the average, the 45% of treated U937 gave rosettes formation.

In the above described conditions, it has been performed the inhibition assay of rosettes formation by using L-PAM, D-PAM, CON-L and CON-D peptides. A further control assay has been carried on by using IgG as inhibition positive control and not derivatized SRBC as negative control.

The results of the assays are shown in Table 4 from which it appears that the peptides L-PAM and D-PAM of the invention are capable of inhibiting rosettes formation between SRBC IgG derivatized and the related receptors on the U937 membrane, as obtained for the IgG. This inhibition is specific since both control SRBC and CON-L and CON-D peptides are unable to inhibit this interaction.

TABLE 4

Rosettes formation inhibition between SRBC-IgG and U937 FcRs

| INHIBITORS | IC50* µg/ml |
|---|---|
| h-IgG | 80 |
| L-PAM | 78 |
| D-PAM | 200 |
| CON-L | No Inhibition |
| CON-D | No Inhibition |
| SRBC | No Inhibition |

*inhibitor amount necessary to reduce at 50% the rosettes formation between SRBC-IgG and U937 FcRs.

The interaction between peptides of formula (I) and class E immunoglobulins has been initially tested by preparation of affinity column and evaluation of their ability to purify IgE from biological fluid. For this purpose, the peptide (I) (5 mg) has been dissolved in 5 ml of 0.1 M sodium bicarbonate buffer pH 9.0 and added to 1.2 g of activated CH-Sepharose resin (Pharmacia, Uppsala, Sweden Cat. n. 17-0490-01), affinity chromatography support preactivated for the direct coupling of peptides and proteins. The suspension has been mixed for 24 hours and the coupling efficiency has been monitored by sampling of reaction mixture at different times and subsequent RP-HPLC analysis. About 90% of starting peptide were covalently bound to the resin after 24 hours. The derivatized resin has been washed with 50 ml of 1 M Tris pH 9.0 and packed on a glass column of 100×6.6 mm I.D. size. For the purification of class E immunoglobulins, the column has been equilibrated with 25 mM BIS-TRIS buffer pH 6.5, at a flow rate of 1 ml/min, monitoring the eluate at 280 nm.

A milliliter of ascitic fluid containing IgE against ovalbumin has been then loaded on the column and after the elution of unbound material, the elution buffer has been changed to 0.1M acetic acid. The material desorbed from this treatment has been collected and analyzed by electrophoretic analysis on polyacrylamide gel. As clearly shown by the electrophoretic analysis, the column has been capable of retaining the immunoglobulinic fraction of the ascitic fluid whereas albumins have not been retained and have been eluted at the column void volume.

The purification capability of compounds of formula (I) prepared either with L or D configuration amino acids has been independent of the type of affinity chromatography support used. In fact, similar results have been obtained with other supports like Protein-Pak supports (Waters, USA), Eupergit C30N (Sigma, USA) and Affi-gel (BioRad, USA).

A further confirmation of the ability of the peptides of formula (I) to bind class E immunoglobulins has been obtained by ELISA determinations. For this purpose a linear binding assay of the formula (I) peptide-IgE specific-biotinilated antigen has been carried on by immobilizing the peptide of formula (I) on microplates for ELISA determinations (Falcon Cat. No. 3912). After conjugation with bovine serum albumin (BSA Sigma Cat. No. A-9418) the peptide of formula (I) has been plated at 50 µg/ml concentration in 0.1M NaHCO$_3$ pH 8.5, 100 µl/well, for 15 hours at 4° C. The plates have been washed 5 times with PBS and the aspecific sites have been saturated by adding in each well 180 µl of a solution containing 3% of powdered milk. After 1 h and 30' at room temperature, the plates have been washed 5 times with PBS-T (PBS-Tween 0.05%) and each well has been filled with 100 µl of a solution of ascitic fluid containing ovalbumin antigen specific IgE at 10 µg/ml concentration in PBS-0.5% powdered milk. After incubation at 37° C. for 1 h and 30' a biotinilated ovalbumin solution of variable concentration among 1 to 30 µg/ml in PBS/0.5% powdered milk has been added, 100 µl/well.

After incubation at 37° C. for 1 h and 30' it has been added (100 µl/well) a solution of peroxidase derivatized streptavidin (Sigma Cat. No. S-5512) diluted in PBS/0.5% powdered milk.

After incubation for 1 h at 37° C., plates have been washed 5 times with PBS-T and each well has been filled with 100 ml of a 2,2'-azino-bis(3-ethylbenzthiazoline-6-sulfonic) acid solution (Sigma Cat. No. A-9941) in citrate phosphate buffer pH 5 and 0.012% hydrogen peroxide.

After about 30 minutes the absorbance of each well has been determined by a plates reader (Merck Mod. Mios) and the results are shown in Table 5. The thus obtained data show that PAM peptide binds E immunoglobulins in a specific and dose dependent manner.

TABLE 5

| IgE (micrograms/ml) | O.D. 450 nm |
|---|---|
| 0 | 0.010 |
| 5 | 0.15 |
| 10 | 0.35 |
| 20 | 0.50 |

Furthermore, it has been evaluated the antiallergic activity in vivo of peptides of this invention.

Rat ascit fluid containing ovalbumin antigen specific IgE and with a total immunoglobulins amount of 4 mg/ml, scaled diluted in PBS, has been injected by intradermal route in a male rat of CD specie.

Intradermal injection of 50 µl volume have been done on the shaved back of the animal.

In this way it has been allowed ascitic fluid IgE to bind FcεR of local mastcells, sensitizing them.

After 24 h, 1 mg of ovalbumin and Evan's Blue dye at 2% concentration in 1 ml of PBS have been injected by endovenous route.

After 15 minutes it has been observed the presence on the rat back derma of a colored area whose extension and color intensity are proportional to the IgE antigen-specific amount injected together with the ascitic fluid.

The blueing lesions are given by the injected antigen that bind to the IgE and determined the degranulation and the release of mediators in the site of intradermal injection. Consequently a local increase of vascular permeability and a dye leak from vessel has been observed.

As a negative control it has been used an intradermal injection (50 µl of PBS free of ascitic fluid) that did not give the formation of blueing lesions.

For the inhibition assay, the ascitic fluid containing IgE and properly diluted has been incubated with L-PAM and D-PAM peptides in total immunoglobulins-peptides molar ratio 1:2,1:20,1:200, 1:2000, 1:20.000, and 1:200.000, that correspond to 26 ng, 260 ng, 2.6 µg, 26 µg, 260 µg, and 2600 µg of L-PAM and D-PAM peptides.

Separate experiments for the two peptides have been performed.

In CD1 rats, 50 µl of the fluid ascitic-peptide mixture at various concentrations have been injected intradermally.

As a positive control it has been used a 50 µl injection of ascitic fluid free of peptide.

After 24 h the antigen, together with Evans's Blue dye, has been injected as described above.

After 15 minutes it has been observed that the intensity and extension of the blueing lesions on the rat back were proportional to the amounts of the injected peptide and were completely absent at highest peptide concentrations.

The results obtained with L-PAM and D-PAM peptides are shown in Table II. These results show that both peptides are able to inhibit in a dose dependent manner the interaction IgE-receptor up to a complete disappearance of the inflammatory reaction.

TABLE 6

| Inhibitor Amount (micrograms) | Extension of blueing lesion (%) D-PAM | Extension of blueing lesion (%) L-PAM |
|---|---|---|
| 0.0 | 100 | 100 |
| 0.025 | 60 | 65 |
| 0.025 | 37 | 50 |
| 2.5 | 33 | 35 |
| 25 | 20 | 0 |
| 250 | 15 | 0 |
| 2500 | 0 | 0 |

What is claimed is:

1. A method of inhibiting the binding of an immunoglobulin (Ig) to a cell surface receptor which binds the Ig comprising administering to a patient in need thereof a peptide of formula I $$(AA_1\text{-}Thr\text{-}AA_2\text{-})_n\text{-}R \quad (I)$$

for a time and under conditions effective to inhibit the binding of said Ig to a cell surface receptor which binds the Ig, wherein said Ig is selected from the group consisting of IgE, IgG and IgA;

Thr is the amino acid threonine, wherein the hydroxyl group is optionally protected with a group conventionally used in peptide chemistry, and wherein threonine is of the D- or L-configuration;

$AA_1$ and $AA_2$ are each tyrosine or arginine,
wherein $AA_1$ and $AA_2$ are different from one another,
wherein the guanidino moiety of arginine is optionally protected with a group conventionally used in peptide chemistry,
wherein tyrosine and arginine are each of the D- or L-configuration,
wherein the α-carbonyl group of $AA_1$ is bonded to the α-amino group of Thr,
wherein the α-carbonyl group of Thr is bonded to the α-amino group of $AA_2$;

n is 2, 3, or 4, and

R is a group to form a dimeric, trimeric or tetrameric peptide.

2. The method according to claim 1, wherein n is 4.

3. The method according to claim 1, wherein each of threonine, tyrosine and arginine is of the D or L configuration.

4. The method according to claim 1, wherein R is a branched tetrapeptide of the formula $(Lys)_2$-Lys-Gly-OH.

5. The method according to claim 1, wherein $AA_1$ is arginine.

6. The method according to claim 1, wherein $AA_2$ is tyrosine.

7. The method according to claim 1, wherein $AA_1$ is Arg(Pmc), wherein "Arg(Pmc)" is $N^G$-2,2,5,7,8-pentamethylchroman-6-sulfonyl arginine.

8. The method according to claim 1, wherein $AA_1$ is Tyr(OtBu), wherein "Tyr(OtBu)" is the tert-butyl ether of tyrosine.

9. The method according to claim 1, wherein the hydroxyl group of threonine is protected with a tert-butyl group.

10. The method according to claim 1, wherein the peptide is administered to said patient at a dose of 1–200 mg peptide per kg body weight per day.

11. The method according to claim 1, wherein the peptide is administered to said patient at a dose of 2–50 mg peptide per kg body weight per day.

12. The method according to claim 1, wherein said Ig is immunoglobulin E (IgE).

13. The method according to claim 1, wherein said Ig is immunoglobulin G (IgG).

14. The method according to claim 1, wherein said Ig is immunoglobulin A (IgA).

* * * * *